US009689753B2

(12) United States Patent
Ramey et al.

(10) Patent No.: US 9,689,753 B2
(45) Date of Patent: Jun. 27, 2017

(54) HANDHELD ANALYTE METER WITH RECHARGING CONTROL FOR IMPROVED ANALYTE TESTING

(71) Applicant: Roche Diabetes Care, Inc., Indianapolis, IN (US)

(72) Inventors: Blaine E. Ramey, Indianapolis, IN (US); Joseph M. Simpson, Fishers, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 562 days.

(21) Appl. No.: 14/285,144

(22) Filed: May 22, 2014

(65) Prior Publication Data
US 2015/0338288 A1  Nov. 26, 2015

(51) Int. Cl.
| | |
|---|---|
| *G01K 7/00* | (2006.01) |
| *G01K 13/00* | (2006.01) |
| *F04B 49/06* | (2006.01) |
| *F04B 51/00* | (2006.01) |
| *G01N 33/66* | (2006.01) |

(Continued)

(52) U.S. Cl.
CPC ............. *G01K 13/00* (2013.01); *F04B 49/06* (2013.01); *F04B 51/00* (2013.01); *G01N 33/48785* (2013.01); *G01N 33/66* (2013.01); *H01M 2/1066* (2013.01); *H01M 10/443* (2013.01); *H01M 10/46* (2013.01); *H02J 7/0042* (2013.01); *H02J 7/0052* (2013.01); *H02J 7/047* (2013.01); *A61B 2560/0204* (2013.01); *H01M 2220/30* (2013.01)

(58) Field of Classification Search
USPC ............ 374/142, 141, 208, 110, 166
See application file for complete search history.

(56) References Cited

U.S. PATENT DOCUMENTS

| | | | | |
|---|---|---|---|---|
| 7,620,437 | B2 * | 11/2009 | Reggiardo | ........... A61B 5/0002 |
| | | | | 204/412 |
| 8,140,294 | B2 | 3/2012 | Ramey et al. | |

(Continued)

OTHER PUBLICATIONS

Life Scan, OneTouch Verio IQ Blood Glucose Monitoring System, Owner's Booklet (2011).

(Continued)

*Primary Examiner* — Mirellys Jagan

(57) ABSTRACT

A handheld analyte meter, such as a blood glucose meter, has a measurement module, a rechargeable battery and a charging control to select a maximum charging current to regulate self-heating during recharging that can interfere with analyte tests. Self-heating by the meter can bias temperature measurements made inside the meter that are used to determine whether the temperature is acceptable for testing. Prior to beginning a charging session, the charging control selects the maximum charging current that does not change during the charging session based capacity of a charging source along with a first temperature measured near the battery that is compared with a first temperature range. By selecting the maximum charging current in this manner, the risk of the measurement module preventing a test under high lock-out conditions and the risk of the measurement module allowing a test when low lock-out conditions that are masked is reduced.

12 Claims, 10 Drawing Sheets

(51) Int. Cl.
*H02J 7/00* (2006.01)
*G01N 33/487* (2006.01)
*H01M 2/10* (2006.01)
*H01M 10/44* (2006.01)
*H01M 10/46* (2006.01)
*H02J 7/04* (2006.01)

(56) References Cited

U.S. PATENT DOCUMENTS

| | | | |
|---|---|---|---|
| 8,441,363 B2 | 5/2013 | Gofman et al. | |
| 2005/0019219 A1* | 1/2005 | Oshiman | G01K 1/16 422/82.12 |
| 2009/0261987 A1* | 10/2009 | Sun | G01N 35/00732 340/870.07 |
| 2012/0094370 A1* | 4/2012 | Ramey | A61B 5/14532 435/288.7 |
| 2012/0095312 A1* | 4/2012 | Ramey | A61B 5/002 600/365 |
| 2012/0142084 A1* | 6/2012 | Dunne | A61B 5/14532 435/287.1 |
| 2013/0108904 A1* | 5/2013 | Okabayashi | H01M 10/486 429/90 |
| 2015/0145467 A1* | 5/2015 | Zhu | G01K 13/00 320/107 |

OTHER PUBLICATIONS

Bayer, Contour USB Glucose Monitoring System User Guide (2009).
Accu-Chek, Inform II Blood Glucose Monitoring System Operator's Manual (2013).

* cited by examiner

HANDHELD ANALYTE METER WITH RECHARGING CONTROL FOR IMPROVED ANALYTE TESTING

FIELD

This disclosure relates to handheld in vitro analyte meters having a rechargeable battery, such as a blood glucose meter or an infusion pump controller with an integral blood glucose meter.

BACKGROUND

Diabetes mellitus, often referred to as diabetes, is a chronic condition in which a person has elevated blood glucose levels that result from the body's inability to produce insulin, use insulin, or both. There are three main types of diabetes. Type 1 diabetes usually strikes children and young adults and is linked to conditions such as autoimmune, genetic, environmental, or a combination. Type 2 diabetes accounts for 90-95% of diabetes cases and is linked to obesity and physical inactivity. Gestational diabetes is a form of glucose intolerance diagnosed during pregnancy and usually resolves soon after delivery.

In 2013, some 382 million people worldwide are estimated to have diabetes, and an estimated 5.1 million people between the ages of 20 and 79 die from diabetes annually, according to the International Diabetes Foundation Diabetes Atlas. In the United States, nearly 24 million Americans have diabetes with an estimated 25 percent of seniors age 60 and older being affected, according to The Centers for Disease Control and Prevention. Diabetes costs are estimated to be $174 billion in the United States alone every year, according to the National Diabetes Information Clearinghouse. Without treatment, diabetes can lead to severe complications such as heart disease, stroke, blindness, kidney failure, amputations, and death related to pneumonia and flu.

Handheld blood glucose meters are used by persons with diabetes to measure blood glucose using a test strip inserted into the meter. The test strip has a collection area on the end of the strip extending from the meter. A small drop of blood is placed on the collection area to initiate an enzymatic reaction to determine a blood glucose measurement. This enzymatic reaction is sensitive to temperature, so an acceptable temperature range is established for preforming accurate blood glucose measurements. Prior to beginning a blood glucose measurement, a temperature sensor typically inside the meter housing measures temperature to determine whether the temperature is within the acceptable temperature range. If the temperature is within the acceptable temperature range, a glucose measurement is performed. If the temperature is outside the acceptable temperature range, a glucose measurement is not performed.

As handheld blood glucose meters have increased in capability with features such as color displays, multiple microprocessors, and wireless communications power consumption has increased leading to the use of rechargeable batteries. During recharging, the charging current and electrochemical reactions cause the battery to self-heat or warm which causes a temperature rise inside the housing or self-heating, particularly during the first hour or two of recharging. When the blood glucose meter rises in temperature, the meter's estimate for the acceptable temperature range to perform a blood glucose test can be inaccurate. Modulating charging current during a recharging session can create self-heating thermal conditions that are difficult to predict. An inaccurate temperature measurement can cause a lock-out condition that prevents a blood glucose measurement from being performed or mask a lock-out condition that inappropriately allows a blood glucose measurement to be performed, potentially for the first hour of recharging. Examples of rechargeable handheld analyte meters include LifeScan, OneTouch Verio IQ Blood Glucose Monitoring System; Bayer, Contour® USB Glucose Monitoring System; and Roche Diagnostics, Accu-Chek® Inform II Blood Glucose Monitoring System.

What is needed is a rechargeable analyte meter with recharging control to manage battery self-heating for improved analyte testing.

SUMMARY

In one embodiment, a handheld analyte meter, such as a blood glucose meter or combination blood glucose meter and infusion pump controller, with recharging control improves analyte testing by regulating self-heating that occurs during recharging and can adversely influence analyte tests. The meter comprises a housing, a cable connector, a rechargeable battery, a main processor, a display, a first temperature sensor, a measurement module, a second temperature sensor, a battery charger, and a charging control. The maximum charging current is selected prior to the beginning of a charging session and the maximum charging current does not change during the charging session. A maximum charging current is selected based upon the capacity of a charging source and a first temperature compared to a first temperature range. By selecting the maximum charging current in this manner, the risk of the measurement module preventing a test under high lock-out conditions and the risk of the measurement module allowing a test when low lock-out conditions are masked is reduced.

In another embodiment, a method for controlling handheld analyte meter, such as a blood glucose meter or combination blood glucose meter and infusion pump controller, recharging improves analyte testing by regulating self-heating that occurs during recharging and can adversely influence analyte tests. The method for controlling meter recharging comprises connecting a cable to a charging source and to the meter, identifying the charging source capacity, measuring a first temperature inside the meter with a first temperature sensor, selecting a maximum charging current, and recharging a rechargeable battery. The maximum charging current is selected prior to the beginning of a charging session and the maximum charging current does not change during the charging session. The maximum charging current is selected based upon the capacity of a charging source and a first temperature compared to a first temperature range. By selecting the maximum charging current in this manner, the risk of the measurement module preventing a test under high lock-out conditions and the risk of the measurement module allowing a test under low lock-out conditions that are masked is reduced.

DETAILED DESCRIPTION

Figure 1:
FIG. 1 shows an a person with diabetes and a health care provider in a clinical environment.

FIG. 1 shows a person with diabetes 10 and a health care provider 12 in a clinical environment 14. A person with diabetes 10 can use a handheld analyte meter such as a blood glucose meter or a combination blood glucose meter and infusion pump controller 16 as part of her therapy. A person with Type 1 diabetes can perform blood glucose measurements seven or more times a day, and the need to perform blood glucose measurement can be urgent for events such as a feeling of low blood glucose, hypoglycemia, and prior to eating for the calculation of an insulin bolus. The health care provider 12 can manage the person with diabetes 10 diagnostic and therapy information using diabetes management programs such as Accu-Chek® 360 Diabetes Management System software and Accu-Chek® Pump Configuration software operating on a computer, accessed via the World Wide Web, or both.

Figure 2:
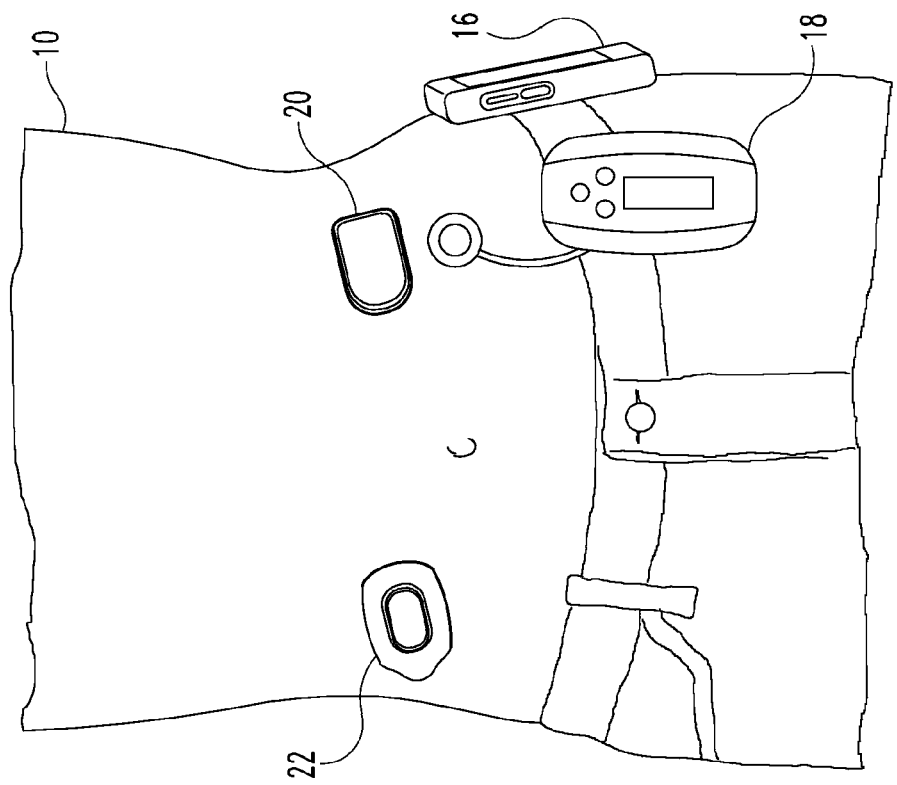
FIG. 2 shows a person with diabetes with a variety of diabetes devices.

FIG. 2 shows a person with diabetes 10 wearing a variety of diabetes devices. The person with diabetes 10 in a self-care environment can use a variety of diabetes devices such as an ambulatory infusion pump 18, a patch infusion pump 20 and adheres to the person's skin, and a continuous glucose monitor 22. These diabetes devices are intended to be used by the person with diabetes 10 during daily activities such as outside under variable seasonal temperatures.

A handheld blood glucose meter or combination handheld blood glucose meter and infusion pump controller 16 is used by persons with diabetes 10 to measure blood glucose. A test strip 24 (FIG. 3), or biosensor, is inserted into the meter 16, and the test strip 24 has a collection area 26 (FIG. 3) on the end of the strip 24 extending from the meter 16. A small drop of blood is placed on the collection area 26 to initiate an enzymatic reaction for electrochemistry or photometric analysis to produce a blood glucose measurement. This enzymatic reaction is sensitive to temperature, so an acceptable temperature range is established for performing accurate blood glucose measurements, such as from about 4° C. to about 45° C. (about 39° F. to about 113° F.). Specific embodiments of the acceptable temperature range are from about 6° C. to about 44° C. (about 43° F. to about 111° F.); 4° C. to about 40° C. (about 39° F. to about 104° F.); and 10° C. to about 45° C. (about 50° F. to about 113° F.) and the like. If the enzymatic reaction occurs outside the acceptable temperature range, the test strip 24 will be operating outside of specifications and could produce an inaccurate blood glucose measurement. Prior to beginning a blood glucose measurement, a temperature sensor located inside the meter 16 housing measures temperature to determine whether the temperature is within the acceptable temperature range. If the temperature is within the acceptable temperature range, a glucose measurement is performed, and, if the temperature is outside the acceptable temperature range, a glucose measurement is not performed.

As handheld analyte meters, such as blood glucose meters and combination blood glucose meters and infusion pump controllers 16, have been enhanced with features such as color displays, multiple microprocessors, and wireless communications power consumption has increased. Increased power consumption also produces internally generated heat that can adversely affect blood glucose measurements. An example of power management to control internal heating in a combination pump controller and blood glucose meter is shown in U.S. Patent Pub. 2012/0095312 A1, Power management for a handheld medical device (Apr. 19, 2012), assigned to Roche Diagnostics Operations, Inc., which is hereby incorporated by reference.

Increased power consumption has also increased battery energy demands leading to the use of rechargeable batteries. Recharging is performed by connecting a cable 56 (FIG. 3) to the analyte meter 16 that supplies power for recharging or by placing the analyte meter 16 configured for inductive charging on a charging pad. During recharging, the charging current and electrochemical reactions cause the battery to self-heat which causes a temperature rise inside the housing. Also during recharging the person with diabetes 10 can have an urgent need to perform a blood glucose test. If the meter 16 is recharging by a cable, the person with diabetes 10 would be required by the meter 16 to disconnect the cable for safety to enable the blood glucose measurement. During this interruption of charging for an urgent blood glucose measurement, battery self-heating can pose the greatest risk for interfering with the blood glucose measurement. When the blood glucose meter 16 rises in temperature, the meter's 16 estimate for the acceptable temperate range to perform a blood glucose test can be inaccurate. An inaccurate temperature measurement can prevent a blood glucose measurement from being performed when the test strip collection area is actually within an acceptable temperature range, e.g., a high lock-out condition caused by battery self-heating. An inaccurate temperature measurement can also permit a blood glucose measurement to be performed when the test strip collection area is outside the acceptable temperature range, e.g., masking a low lock-out condition caused by battery self-heating.

Figure 3:
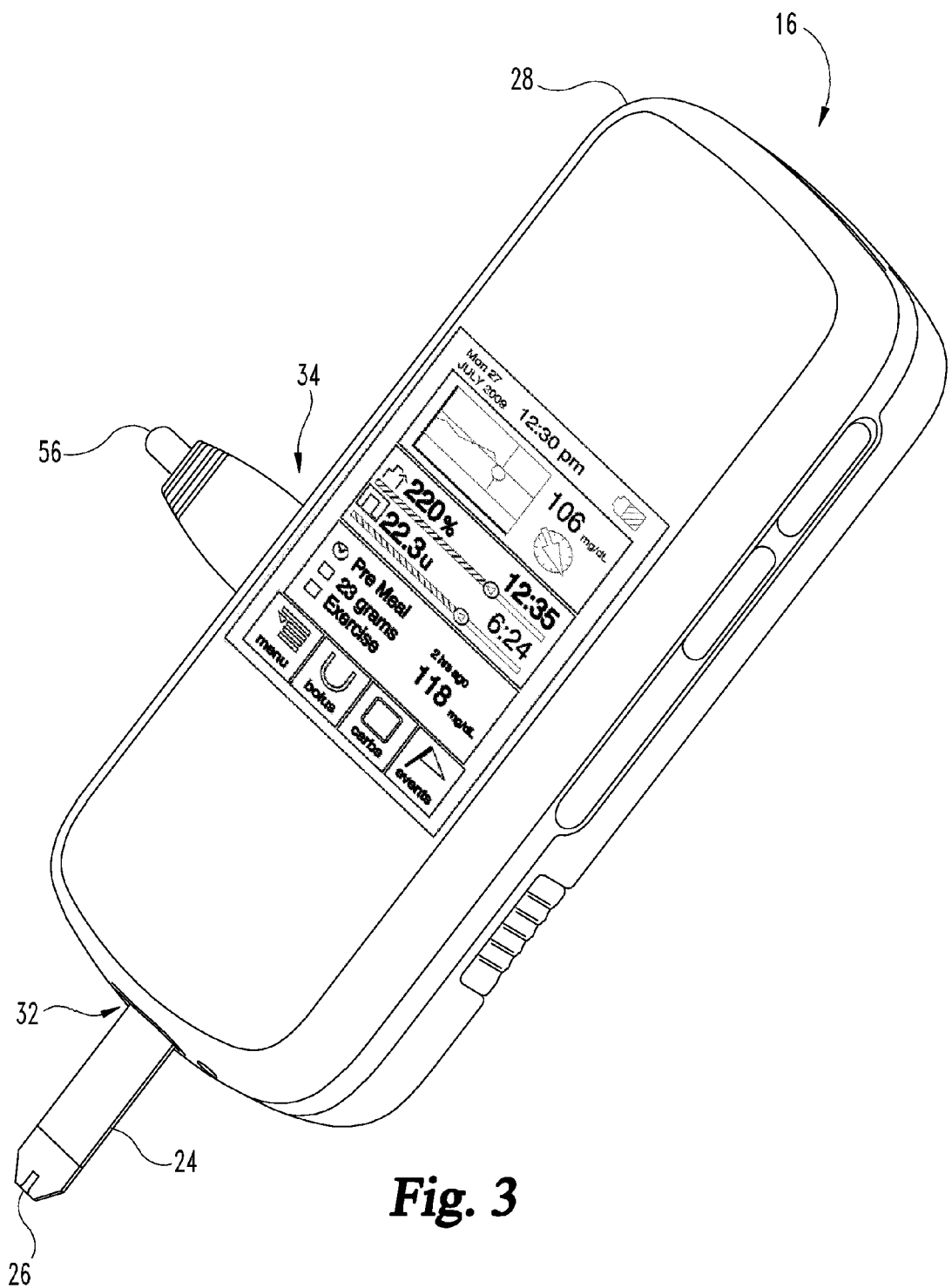
FIG. 3 shows a perspective view of a handheld analyte meter with a rechargeable battery.
Figure 4:
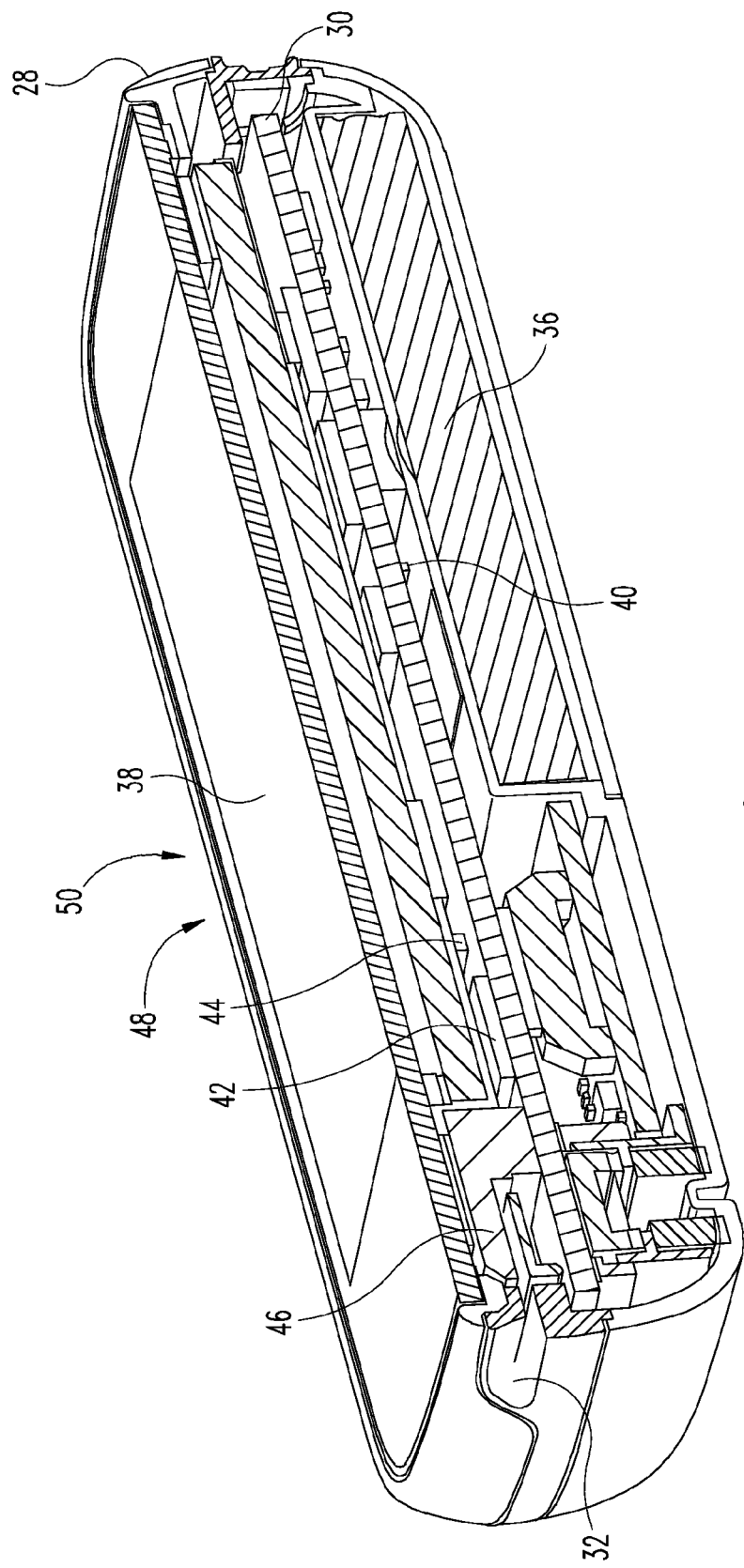
FIG. 4 shows a perspective cut-away view of a handheld analyte meter with a rechargeable battery.

FIG. 3 shows a perspective view of a handheld analyte meter 16 with a rechargeable battery, and FIG. 4 shows a perspective cut-away view of the handheld analyte meter 16 with a rechargeable battery. The handheld analyte meter with recharging control for controlling self-heating to improve analyte testing comprises a housing 28, a cable connector 34, a rechargeable battery 36, a display 38, a first temperature sensor 40, a measurement module 42, a second temperature sensor 44, a strip connector 46, a battery charger 48, and a charging control 50.

The housing 28 is formed from a thermoplastic that both encloses handheld analyte meter 16 components and serves as a frame for carrying components. The housing 28 is substantially sealed except for the strip port 32 that is open to receive a test strip 24 and some airflow can occur through the strip port 32 to the housing interior. The cable connector 34 is carried in the housing 28 with a first end 52 (FIG. 6) exposed outside the housing for connecting to a charging source and a second end 54 (FIG. 6) coupled the circuit board 30. The cable connector 34 is used to for both communications and recharging and can be a Universal Serial Bus (USB) mini connector and the like. When a cable 56 is attached to the cable connector 34 for recharging, the battery charger 48 can determine both the type and capacity of the power source for recharging. The general types of power sources available are a dedicated power source and a USB power source such as can be found on a computer USB port. Both the dedicated power source and auxiliary power source for USB have an available charging current of 500 mA; however, the auxiliary power source often limits charging current to below 500 mA due to constraints such as other power requirements. The rechargeable battery 36 is carried inside the housing 28 and is coupled to the circuit board 30 and to the cable connector second end 54. During recharging the rechargeable battery 36 self-heats due to electrochemical reactions associated with recharging along with electrical impedance associated with the charging current. Heat rise generated by the rechargeable battery during recharging ranges from about 2° C. to about 4° C. (about 3.6° F. to about 7.2° F.) depending upon the charging current. The rechargeable battery 36 can be a lithium ion battery rated at 3.7 VDC and 1150 mAh and has a predetermined charge level in the range from about 300 mA to about 1150 mA such as less than about 450 mA.

Figure 5:
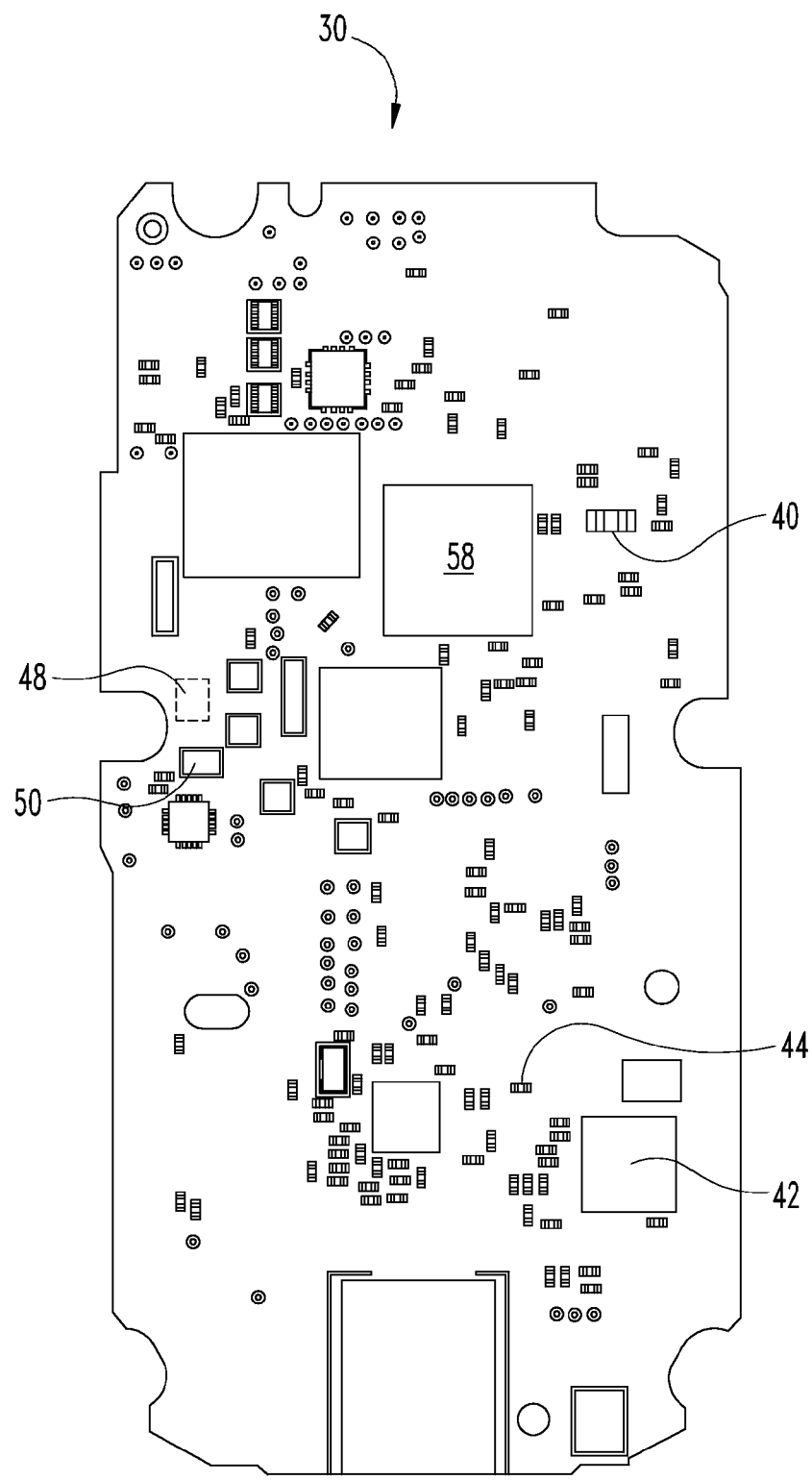
FIG. 5 shows a printed circuit board for a handheld analyte meter with a rechargeable battery.

FIG. 5 shows a printed circuit board 30 for a handheld analyte meter 16 with a rechargeable battery 36. The spatial relationship is shown among the main processor 58, first temperature sensor 40, measurement module 42, and second temperature sensor 44. Additionally shown are the battery charger 48 and charging control 50.

Figure 6:
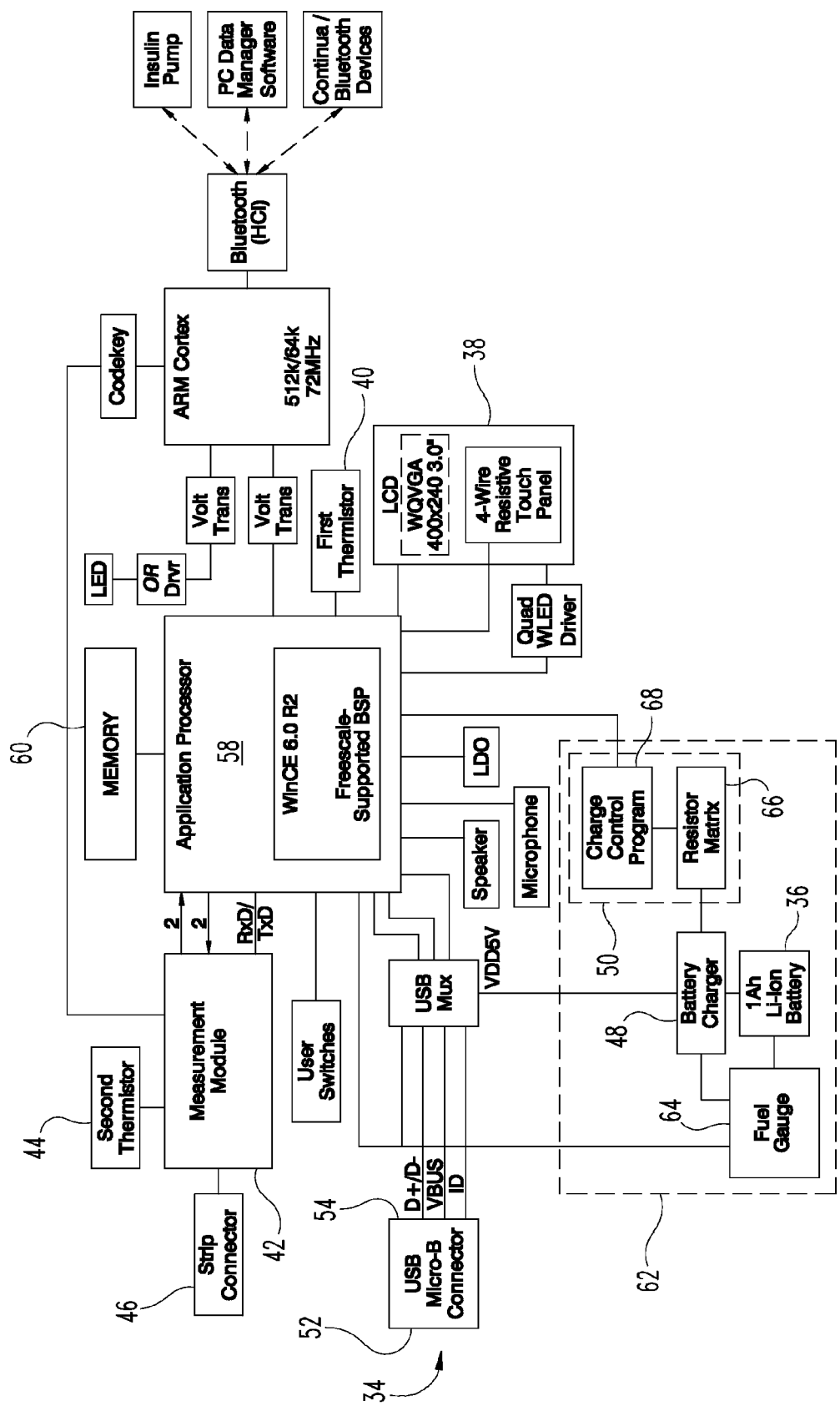
FIG. 6 shows a block diagram of a handheld analyte meter with a rechargeable battery.

FIG. 6 shows a block diagram of a handheld analyte meter 16 with a rechargeable battery 36. The handheld analyte meter 16 comprises a housing (not shown), a cable connector 34, a rechargeable battery 36, a main processor 58 with memory 60, a display 38, a first temperature sensor 40, a measurement module 42, a second temperature sensor 44, a strip connector 46, and charging module 62 comprising a battery charger 48 and a charging control 50. The main processor 58, also known as the user interface processor, can be a Freescale i.MX233 application processor using an operating system such as Microsoft WinCE. Memory 60 coupled to the process can be both volatile Synchronous Dynamic Random Access Memory (SDRAM) and non-volatile flash memory. The display 38 can be a liquid crystal display (LCD) having a resistive touch panel overlaid that cooperates with the display to form user interface buttons.

The first temperature sensor 40 can be a thermistor and is carried on the circuit board 30 near the main processor 58 and rechargeable battery 36. The first temperature sensor 40 is used for measuring a first temperature inside the housing 28 prior to beginning a charging session that is compared to a first temperature range. The first temperature range is selected to balance self-heating against charging time such as in the range from about 18° C. to about 27° C. (about 64° F. to about 81° F.).

The measurement module 42, sometimes referred to as a measurement engine, is carried on the circuit board 30 near the test strip port 32 and coupled to the main processor 58, the second temperature sensor 44, and a strip connector 46. The measurement module 42 can be an Application Specific Integrated Circuit (ASIC) with a module processor and module memory that contains measurement firmware that perform the electrochemistry or photometric analysis of the test strip 24 once a blood sample has been applied to product a blood glucose measurement. The measurement module 42 also directly controls the second temperature sensor 44. The measurement module 42 determines high lock-out and low lock-out conditions to prevent blood glucose measurements based upon the second temperature of the second temperature sensor 44. The measurement module 42 determines a high lock-out condition when the temperature as measured by the second temperature sensor 44 is higher than the specific range for the enzymatic reaction such as above about 45° C. (113° F.) or in other embodiments about 44° C. (about 111° F.), and 40° C. (about 104° F.). The measurement module 42 determines a low lock-out condition when the temperature measured by the second temperature sensor 44 is lower than the specific range for the enzymatic reaction such as lower than about 4° C. (39° F.) or in other embodiments about 6° C. (about 43° F.), and about 10° C. (about 50° F. The temperature range between the low lock-out and high lock-out is the acceptable temperature range as measured by the second temperature sensor 44 for performing blood glucose measurements, which is about 4° C. to about 45° C. (about 39° F. to about 113° F.). Specific embodiments of the acceptable temperature range are from about 6° C. to about 44° C. (about 43° F. to about 111° F.); 4° C. to about 40° C. (about 39° F. to about 104° F.); and 10° C. to about 45° C. (about 50° F. to about 113° F.) and the like.

During recharging, battery 36 self-heating can potentially create a false high-lock out condition to prevent performing a blood glucose measurement when the test strip 24 is actually within the acceptable temperature range to perform a blood glucose measurement. Also during recharging, battery 36 self-heating can potentially mask a low lock-out condition that would permit performing a blood glucose measurement when the actual test strip 24 temperature is lower than the acceptable temperature range to perform a blood glucose measurement. If a low lock-out condition is masked by battery 36 self-heating, a person with diabetes 10 could perform a blood glucose measurement outside of the specifications for the test strip 24. This blood glucose measurement performed outside of test strip 24 specifications could then be used for a therapy adjustment such as delivering an insulin bolus with unpredictable results.

The second temperature sensor 44 can be a thermistor carried on the circuit board 30 near the measurement module 42 for measuring a second temperature inside the housing 28. By locating the second temperature sensor 44 near the measurement module 42, the second temperature 44 more closely reflects the test strip 24 temperature than the first temperature sensor 40 that more closely reflects the battery 36 temperature. The measurement module 42 controls the second temperature sensor 44. Prior to beginning an analyte test, the measurement module 42 obtains a second temperature from the second temperature sensor 44, and the second temperature is compared to a second temperature range. The second temperature range is the test strip 24 specified temperature operating range such as from about 6° C. to about 44° C. (about 43° F. to about 111° F.). The measurement module 42 compares the second temperature to the second temperature range to determine whether to impose a high lock-out or low-lock out to prevent a blood glucose measurement from being conducted because the test strip 24 temperature could be outside its specified temperature range.

The strip connector 46 is carried on the circuit board 30 near the test strip port 32. The strip connector 46 is coupled to the measurement module 42 and configured to receive a test strip 24. When the test strip 24 is inserted through the strip port 32 into the strip connector 46, test strip 24 contacts form an electrical connection with strip connector 46 terminals and to the measurement module 42. There is little thermal conduction between the test strip 24 and the strip connector 46 because the test strip 24 substrate is plastic. The charging module 62 is discussed below.

Figure 7:
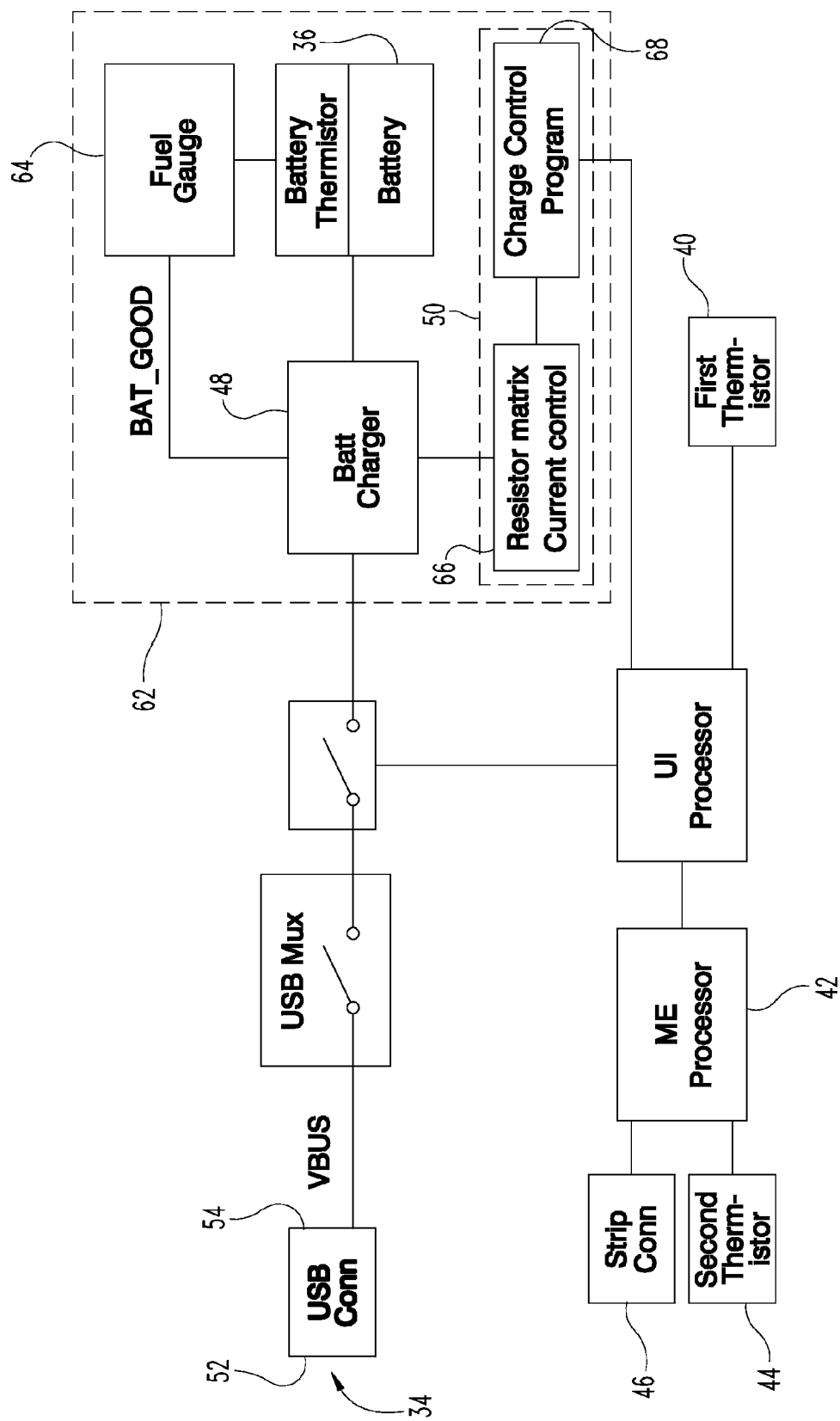
FIG. 7 shows a block diagram of a charging module comprising a battery charger and charging control program for a handheld analyte meter with a rechargeable battery.

FIG. 7 shows a block diagram of a charging module 62 comprising a battery charger 48, charging control 50, fuel gauge 64, and rechargeable battery 36. The battery charger 48 is carried on the circuit board 30 and coupled to the cable connector 34 that charges the rechargeable battery 36 up to a maximum charging current until the rechargeable battery 36 reaches a predetermined charge level. The battery charger 48 is also coupled to fuel gauge 64. The battery charger 48 receives 5 VDC from the USB port and converts it to 4.2 VDC for charging the battery 36, and the charging current is also controlled by the battery charger 48. The fuel gauge 64 provides a battery 36 temperature lock-out for charging to prevent damage to the battery. The battery 36 temperature charging acceptance range is wide enough, so it does not interact with the high lock-out and low lock-out. The charging control 50 comprises a charging resistor matrix 66 and charge control program 68. The charging resistor matrix 66 is used to change the control voltage of the battery charger 48 to limit charging current. The charging control 50 is carried on the circuit board 30 and coupled to the battery charger 48 that prior to the beginning of a charging session selects the maximum charging current that does not change during the charging session. The maximum charging current is selected based upon capacity of a charging source and the first temperature compared to the first temperature range. The maximum charging current can be in the range from about 50 mA to about 450 mA such as a discrete value selected from one of 50 mA, 220 mA, 300 mA, 380 mA, and 450 mA.

Figure 8:
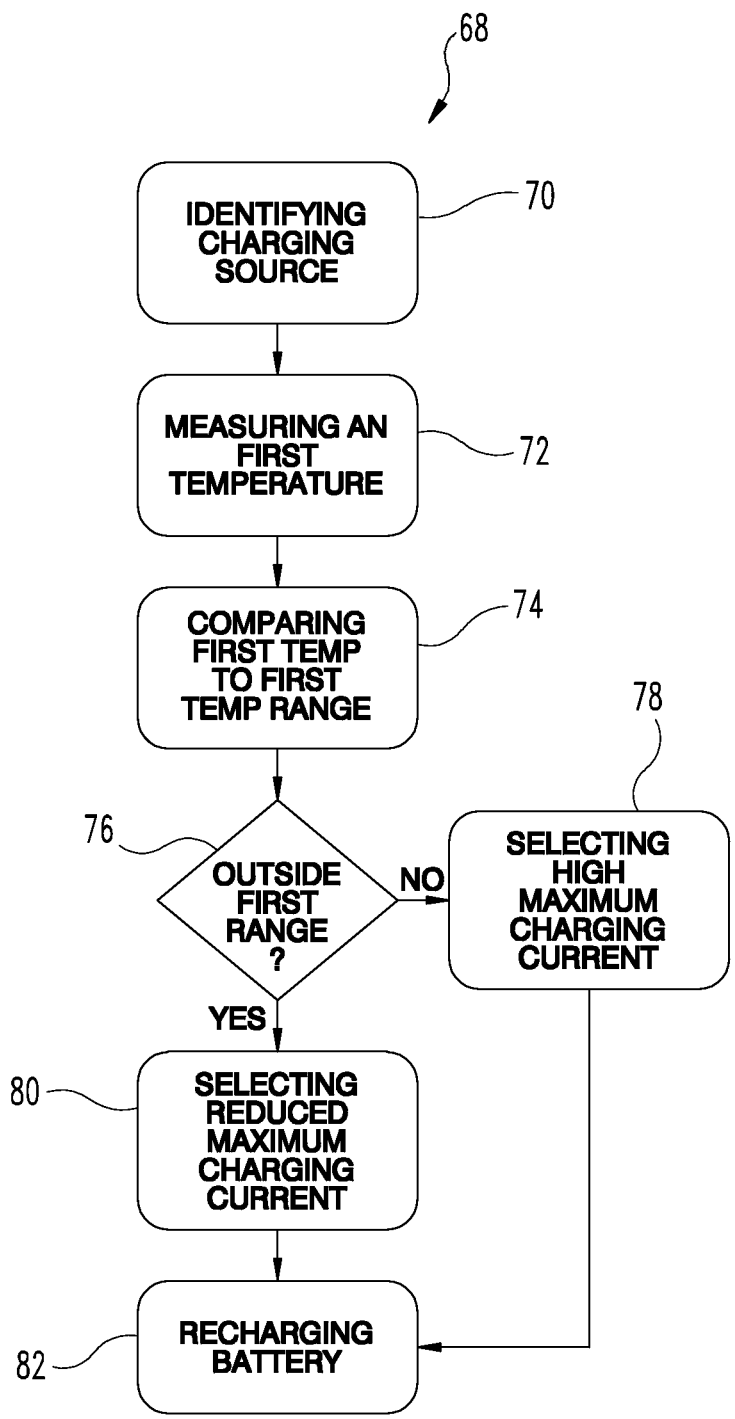
FIG. 8 shows a flowchart of a charge control program for selecting a charge current for the battery charger.

FIG. 8 shows a flowchart of a charge control program 68 for selecting a charge current for the battery charger. The charge control program 68 is stored in memory 60 and executed by the main processor 58. The charge control program 68 comprises the steps of identifying the charging source 70, measuring a first temperature 72, comparing the first temperature to a first temperature range 74, determining whether the first temperature is outside the first temperature range 76, selecting high maximum charging current 78 if the first temperature is not outside the first temperature range, and selected reduced maximum charging current 80 if the first temperature is outside the first temperature range, and charging the battery 82. When a charging source is plugged into the cable connector 52, the battery charger 48 determines whether the charging source is a dedicated charger or a charging source from a device such as a computer. Dedicated charging sources typically have a capacity of at least 500 mA. Device charging sources such as a computer typically have a capacity of 100 mA to 500 mA. The first temperature is read to determine the temperature inside the housing. This first temperature is compared against a first temperature range that is selected to balance self-heating against charging time such as in the range from about 18° C. to about 27° C. (about 64° F. to about 81° F.). If the first temperature is within the first temperature range, the charge control program will select a highest maximum charging current of 500 mA or less such as 380 mA. If the first temperature is outside the first temperature range, the charge control program will select a reduced maximum charging current that is under 380 mA, such as 300 mA, 220 mA, or 50 mA.

Figure 9:
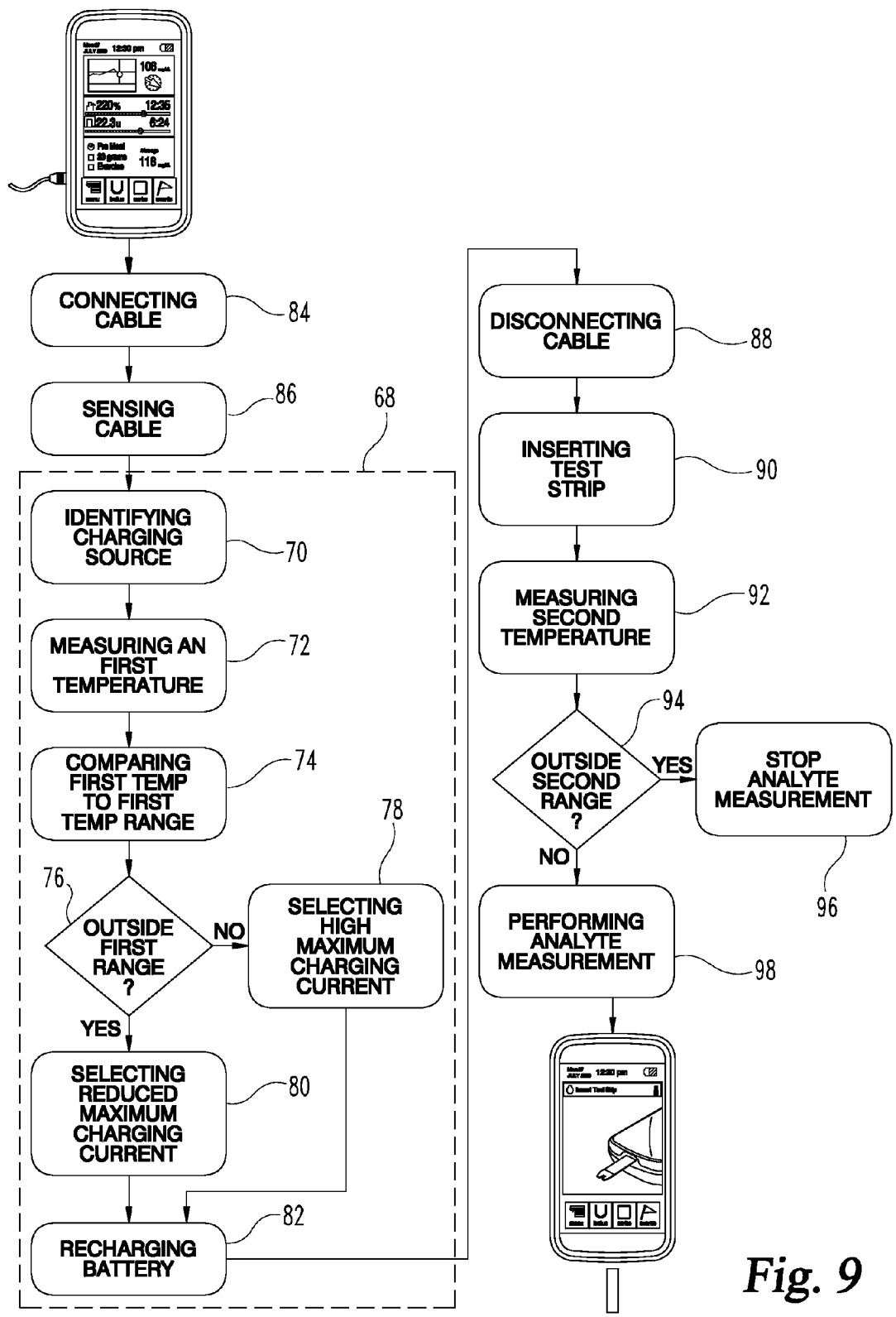
FIG. 9 shows a flowchart of a method for recharging a handheld analyte meter with a rechargeable battery.

FIG. 9 shows a flowchart of a method for recharging a handheld analyte meter 16 with a rechargeable battery 36. The method comprises the steps of connecting a cable 84, sensing the cable 86, identifying the charging source 70, measuring a first temperature 72, determining whether the first temperature was outside a first temperature range 76, selecting a high maximum charging current 78 if the first temperature is not outside the first temperature range, selecting a reduced maximum charging current 80, recharging a rechargeable battery 82, disconnecting the cable 88, inserting a test strip 90, measuring a second temperature 92, determining whether the second temperature is within a second temperature range 94, stopping analyte measurement 96 if the second temperature is outside the second temperature range, and performing the analyte test 98 if the second temperature is within the second temperature range.

To prepare for recharging, the user connects a cable 84 that is coupled to a charging source to a cable connector 52 on the handheld analyte meter 16, and the user turns the analyte meter 16 "on" if it was "off." The cable 56 provides both power and communications such as a USB cable. The analyte meter 16 senses 86 when the cable 56 is connected to the cable connector 52 and disables the analyte meter 16 from conducting an analyte test for electrical safety. The analyte meter 16 also identifies the type of charging source 70 and the charging source capacity.

Prior to beginning a recharging session, the analyte meter 16 measures a first temperature in the analyte meter 16 with a first temperature sensor 40 located inside the analyte meter housing 28 near the rechargeable battery 36. The analyte meter 16 determines whether the first temperature is outside a first temperature range to reduce the maximum charging current. The first temperature range is selected to balance self-heating against charging time such as in the range from about 18° C. to about 27° C. (about 64° F. to about 81° F.).

A maximum charging current is selected prior to the beginning of a charging session that does not change during the charging session. The maximum charging current is selected based upon capacity of a charging source and the first temperature compared to the first temperature range in the range from about 50 mA to about 380 mA such as one of the discrete values of 50 mA, 220 mA, 300 mA, 380 mA, and 450 mA. Although the maximum charging current is selected the actual charging current can be zero because the fuel gauge 64 provides a battery 36 temperature lock-out to prevent damage to the battery 36. If the battery 36 temperature is too high, the battery charger 62 will disable charging to avoid damaging the battery 36. The maximum charging current does not change during the charging session because the maximum charging current is selected to avoid self-heating that would create a high lock-out condition or mask a low-lock out condition. If the first temperature is within the first temperature range, the charge control program 50 will select a high maximum charging current of 500 mA or less such as 380 mA. If the first temperature is outside the first temperature range, the charge control program 50 will select a reduced maximum charging current that is under 380 mA, such as 300 mA, 220 mA, or 50 mA. After the maximum charging current is selected, the recharging session begins by recharging the rechargeable battery 36 of the analyte meter 16 at up to the maximum charging current selected.

When the recharging session is completed or if the user desires to interrupt the recharging session to perform an analyte test, such as an urgent blood glucose measurement due to feelings of hypoglycemia or to calculate an insulin bolus. The user disconnects the cable 56 from the analyte meter 16. The analyte meter 16 is now enabled to perform an analyte test such as a blood glucose measurement. The user inserts a test strip 24 into a strip port 32 on the analyte meter 16, and the measurement module 42 is activated to measure the second temperature with the second temperature 44 sensor located inside the analyte meter housing 28 near the measurement module 42. The measurement module 42 determines whether the second temperature measurement is within a second temperature range to conduct an analyte test. The analyte meter 16 then performs the analyte test if the second temperature is within the second temperature range. The analyte meter will report an error if the second temperature is outside the second temperature range.

Figure 10:
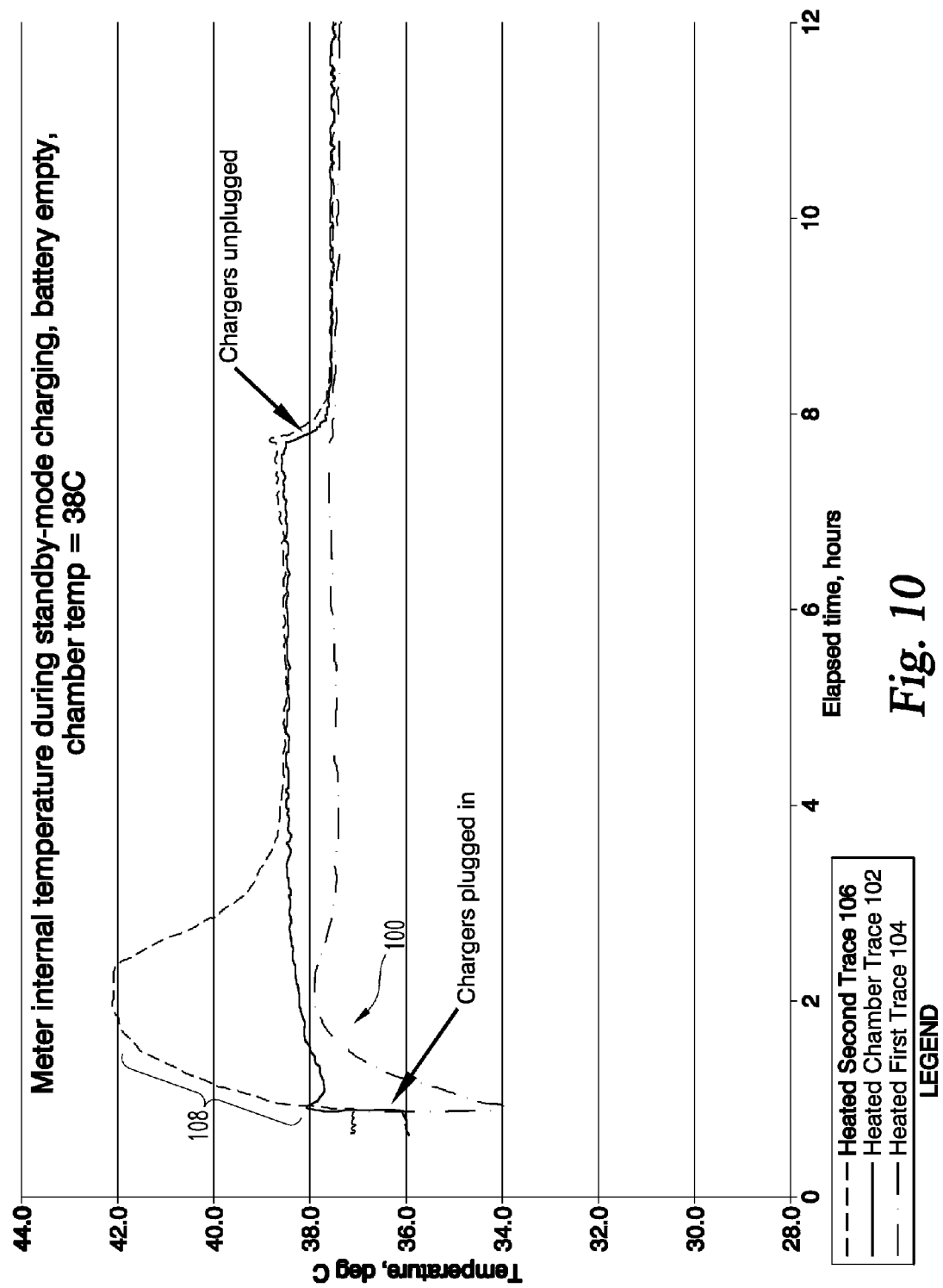
FIG. 10 shows test results from a heated environmental chamber comparing a handheld analyte meter with a charging control and a handheld analyte meter without charging control during recharging.

FIG. 10 shows test results in a heated environmental chamber comparing temperature increases during recharging for a handheld analyte meter with charging control 16 (first analyte meter) and a handheld analyte meter without charging control (second analyte meter). The environment chamber was heated to 38° C. (100° F.), and the first analyte meter 16 and the second analyte meter were placed in the environmental chamber. To measure temperatures that could cause the measurement module 42 to impose a high lock-out condition or a low lock-out condition, a thermocouple was attached by a thermally conductive adhesive to the second temperature sensor of each of the first analyte meter 16 and the second analyte meter. A third thermocouple was placed in the environmental chamber to measure internal chamber temperature as shown by the heated chamber trace.

The testing procedure began with opening environment chamber door to plug in a USB cable with a dedicated charger to each meter's cable connector. Opening the environmental chamber door caused a temporary transient temperature decrease of about 4° C. (7.2° F.) as shown by the heated chamber trace. The first analyte meter 16 is shown in the test results as a heated first trace, and the second analyte meter is shown in the test results as a heated second trace. As the meters are allowed to charge over several hours, the temperature characteristics were observed. The second analyte meter, without the charging control program, charged at 380 mA, and experienced an initial temperature rise of about 4° C. compared to the first analyte meter 16, with the charging control program 50. The initial temperature rise on the second analyte meter without the charge control program would have caused a high lock-out condition, and incorrectly prevented the second analyte meter because the heated chamber trace shows the test strip temperature would have been within an acceptable temperature range to perform a blood glucose test. The first analyte meter 16 with the charge control program 50 charged at 220 mA, and the heated first trace shows that the first analyte meter did not enter a high lock-out condition during the entire test.

Figure 11:
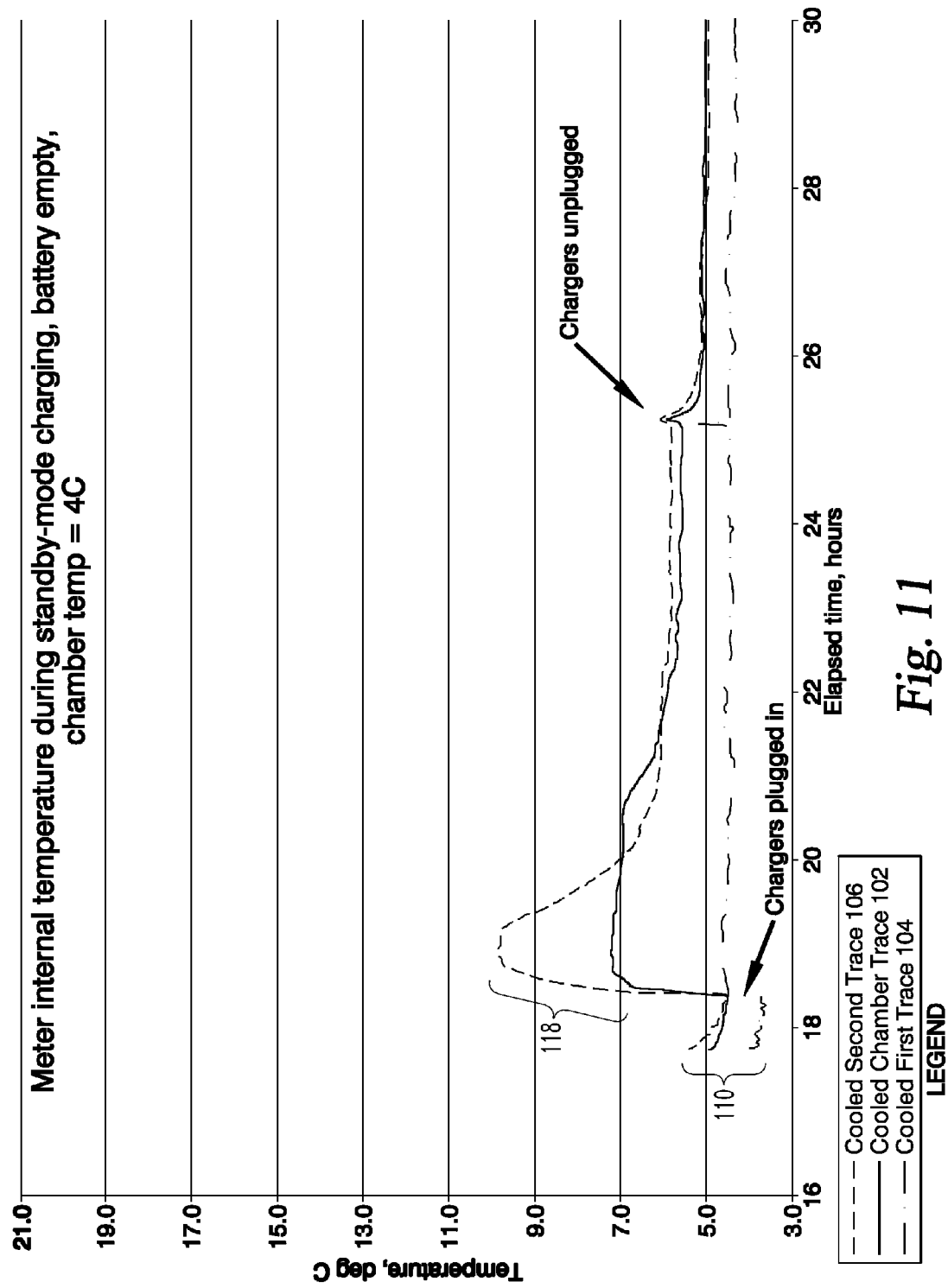
FIG. 11 shows test results from a cooled environmental chamber comparing a handheld analyte meter with a charging control and a handheld analyte meter without charging control during recharging.

FIG. 11 shows test results in a cooled environmental chamber comparing temperature increases during recharging for a handheld analyte meter with charging control 16 (first analyte meter) and a handheld analyte meter without charging control (second analyte meter). The environment chamber was cooled to 4° C. (39.2° F.), and the first analyte meter 16 and the second analyte meters were placed in the environmental chamber. To measure temperatures that could cause the measurement module 42 to impose a high lock-out condition or a low lock-out condition, a thermocouple was attached by a thermally conductive adhesive to the second temperature sensor of the first analyte meter 16 and the second analyte meter. A third thermocouple was placed in the environmental chamber to measure interval chamber temperature as shown by the cooled chamber trace.

The testing procedure began with opening environment chamber door to plug in a USB cable with a dedicated charger to each meter's cable connector. Opening the environmental chamber door caused a temporary transient temperature increase of about 3° C. (5.4° F.) as shown by the cooled chamber trace. The first analyte meter 16 is shown in the test results as a cooled first trace, and the second analyte meter is shown in the test results as a cooled second trace. As the meters are allowed to charge over several hours, their temperature characteristics were observed. The second analyte meter without the charge control program charged at 380 mA and experienced an initial temperature rise of about 4° C. (10.8° F.) compared to the first analyte meter with the charge control program. The initial temperature rise on the second analyte meter would have masked a low lock-out condition, and incorrectly allowed a blood glucose test to be performed despite the strip temperature being too low as shown by the cooled chamber trace. The first analyte meter with the charge control program charged at 220 mA and did not mask a low lock-out condition during the entire test.

Thus, embodiments of the handheld analyte meter with charging control for improved analyte testing are disclosed. One skilled in the art will appreciate that the teachings can be practiced with embodiments other than those disclosed. The disclosed embodiments are presented for purposes of illustration and not limitation, and the invention is only limited by the claims that follow.

What is claimed is:

1. A handheld analyte meter with recharging control for regulating self-heating to improve analyte testing, comprising:
   a housing having a circuit board carried inside the housing and a test strip port;
   a cable connector carried in the housing with a first end exposed outside the housing for connection to a charging source and a second end coupled to the circuit board;
   a rechargeable battery carried inside the housing and coupled to the circuit board and coupled to the cable connector second end;
   a main processor carried on the circuit board and coupled to the rechargeable battery, the main processor having memory;
   a display coupled to the circuit board and the main processor;
   a first temperature sensor carried on the circuit board near the main processor and rechargeable battery for measuring a first temperature inside the housing prior to beginning a charging session that is compared to a first temperature range;
   a measurement module carried on the circuit board near the test strip port and coupled to the main processor;
   a second temperature sensor carried on the circuit board near the measurement module for measuring a second temperature inside the housing prior to beginning an analyte test that is compared to a second temperature range;
   a strip connector carried on the circuit board near the test strip port, the strip connector coupled to the measurement module and configured to receive a test strip;
   a battery charger carried on the circuit board and coupled to the cable connector that charges the rechargeable battery up to a maximum charging current until the rechargeable battery reaches a predetermined charge level; and
   a charging control carried on the circuit board and coupled to the battery charger that prior to the beginning of a charging session selects the maximum charging current that does not change during the charging session,
      if the first temperature is within the first temperature range, the charging control selects a high maximum charging current for the maximum charging current, and if the first temperature is outside the first temperature range, the charging control selects a reduced maximum charging current for the maximum charging current.

2. The handheld analyte meter of claim 1, wherein if the first temperature is lower than the first temperature range the maximum charging current is reduced to lower the risk of masking a low lock-out that permits an analyte test when the second temperature is higher than a lowest value of the second temperature range.

3. The handheld analyte meter of claim 1, wherein the test strip has a strip temperature range from about 4° C. to about 45° C.

4. The handheld analyte meter of claim 1, wherein the handheld rechargeable analyte meter is selected from one of a handheld infusion pump controller with blood glucose meter and self-testing blood glucose meter.

5. The handheld analyte meter of claim 1, wherein if the first temperature is higher than the first temperature range the maximum charging current is reduced to lower the risk of a high lock-out that prevents an analyte test when the second temperature is higher than the second temperature range.

6. The handheld analyte meter of claim 5, wherein the charging current is selected in the range from about 50 mA to about 450 mA.

7. A method for controlling handheld analyte meter recharging to regulate self-heating for improved analyte testing, comprising:
   connecting a cable coupled to a charging source to a cable connector on the handheld analyte meter and turning the analyte meter on if the analyte meter was off when the cable is connected to the cable connector;
   sensing the cable is connected to the cable connector and disabling the analyte meter from conducting an analyte test for safety;
   identifying a capacity of the charging source by the analyte meter;
   measuring a first temperature in the analyte meter with a first temperature sensor located inside an analyte meter housing near a rechargeable battery prior to a beginning of a charging session;
   determining whether the first temperature is within a first temperature range;
   selecting a high maximum charging current for a maximum charging current prior to the beginning of the charging session that does not change during the charging session based upon the capacity of the charging source and if the first temperature is within the first temperature range;
   selecting a reduced maximum charging current for the maximum charging current prior to the beginning of the charging session that does not change during the charging session based upon the capacity of the charging source and if the first temperature is outside the first temperature range;
   recharging the rechargeable battery of the analyte meter at up to the maximum charging current selected;
   disconnecting the cable from the analyte meter and enabling the analyte meter to perform an analyte test;
   inserting a test strip into a strip port on the analyte meter;
   measuring a second temperature with a second temperature sensor located inside the analyte meter housing near a measurement engine;
   determining whether the second temperature measurement is within a second temperature range to conduct the analyte test; and
   performing the analyte test if the second temperature is within the second temperature range.

8. The method of claim 7, wherein if the first temperature is higher than the first temperature range the maximum charging current is reduced to lower a risk of a high lock-out that prevents an analyte test when the second temperature is higher than the second temperature range.

9. The method of claim 7, wherein if the first temperature is lower than the first temperature range maximum charging current is reduced to lower a risk of masking a low lock-out that permits an analyte test when the second temperature is higher than a lowest value of the second temperature range.

10. The method of claim 7, wherein the charging current is selected in the range from about 50 mA to about 450 mA.

11. The method of claim 7, wherein the test strip has a strip temperature range from about 4° C. to about 45° C.

12. The method of claim 7 wherein the handheld analyte meter is selected from one of a handheld infusion pump controller with blood glucose meter and a handheld blood glucose meter.

* * * * *